(12) United States Patent
Hayoz et al.

(10) Patent No.: US 11,147,670 B2
(45) Date of Patent: Oct. 19, 2021

(54) ANNULOPLASTY SYSTEM AND A METHOD FOR MONITORING THE EFFECTIVENESS OF AN ANNULOPLASTY TREATMENT

(71) Applicant: KEPHALIOS S.A.S., Paris (FR)

(72) Inventors: Daniel Hayoz, Villars-sur-Glâne (CH); Enrico Fermi, Paris (FR); Daniele Zanotti, Aix en Provence (FR)

(73) Assignee: KEPHALIOS S.A.S., Aix-en-Provence (FR)

( * ) Notice: Subject to any disclaimer, the term of this patent is extended or adjusted under 35 U.S.C. 154(b) by 73 days.

(21) Appl. No.: 15/569,813

(22) PCT Filed: Apr. 29, 2016

(86) PCT No.: PCT/EP2016/059623
§ 371 (c)(1),
(2) Date: Oct. 27, 2017

(87) PCT Pub. No.: WO2016/174210
PCT Pub. Date: Nov. 3, 2016

(65) Prior Publication Data
US 2018/0140420 A1   May 24, 2018

(30) Foreign Application Priority Data
Apr. 29, 2015   (EP) ...................... 15165726

(51) Int. Cl.
*A61F 2/24*        (2006.01)
*A61B 5/00*        (2006.01)
(Continued)

(52) U.S. Cl.
CPC ............. *A61F 2/2445* (2013.01); *A61B 5/029* (2013.01); *A61B 5/686* (2013.01); *A61B 8/06* (2013.01);
(Continued)

(58) Field of Classification Search
CPC .................. A61F 2/2409; A61F 2/2466; A61F 2250/0002; A61F 2250/0004;
(Continued)

(56) References Cited

U.S. PATENT DOCUMENTS 6,398,734 B1   6/2002   Cimochowski et al.
6,406,493 B1   6/2002   Tu et al.
(Continued)

FOREIGN PATENT DOCUMENTS

EP        2 468 215 A1     6/2012
WO     2006/012013 A2      2/2006
(Continued)

OTHER PUBLICATIONS http://mspde.usc.edu/inspiring/resource/energy%20interaction/Electrical/human%20E&M%204.pdf (Year: 2014).*
(Continued)

*Primary Examiner* — Brian A Dukert
*Assistant Examiner* — Rebecca Lynee Zimmerman
(74) *Attorney, Agent, or Firm* — Finch & Maloney, PLLC; Michael J. Bujold; Jay S. Franklin

(57) ABSTRACT

An annuloplasty system is provided which comprises an annuloplasty ring assembly (2), at least one sensor (8) and an external monitor (5) or a prompting device. The annuloplasty ring assembly (2) has an interface adapted to establish an operative connection with a manipulator. The manipulator is utilized for manipulating the annuloplasty ring assembly (2). The sensor (8) is configured to detect regurgitation (13, 34). The external monitor (5) or the prompting device is adapted to provide, e.g. display, information based on the detected regurgitation (13, 34).

10 Claims, 7 Drawing Sheets

Figure 1:
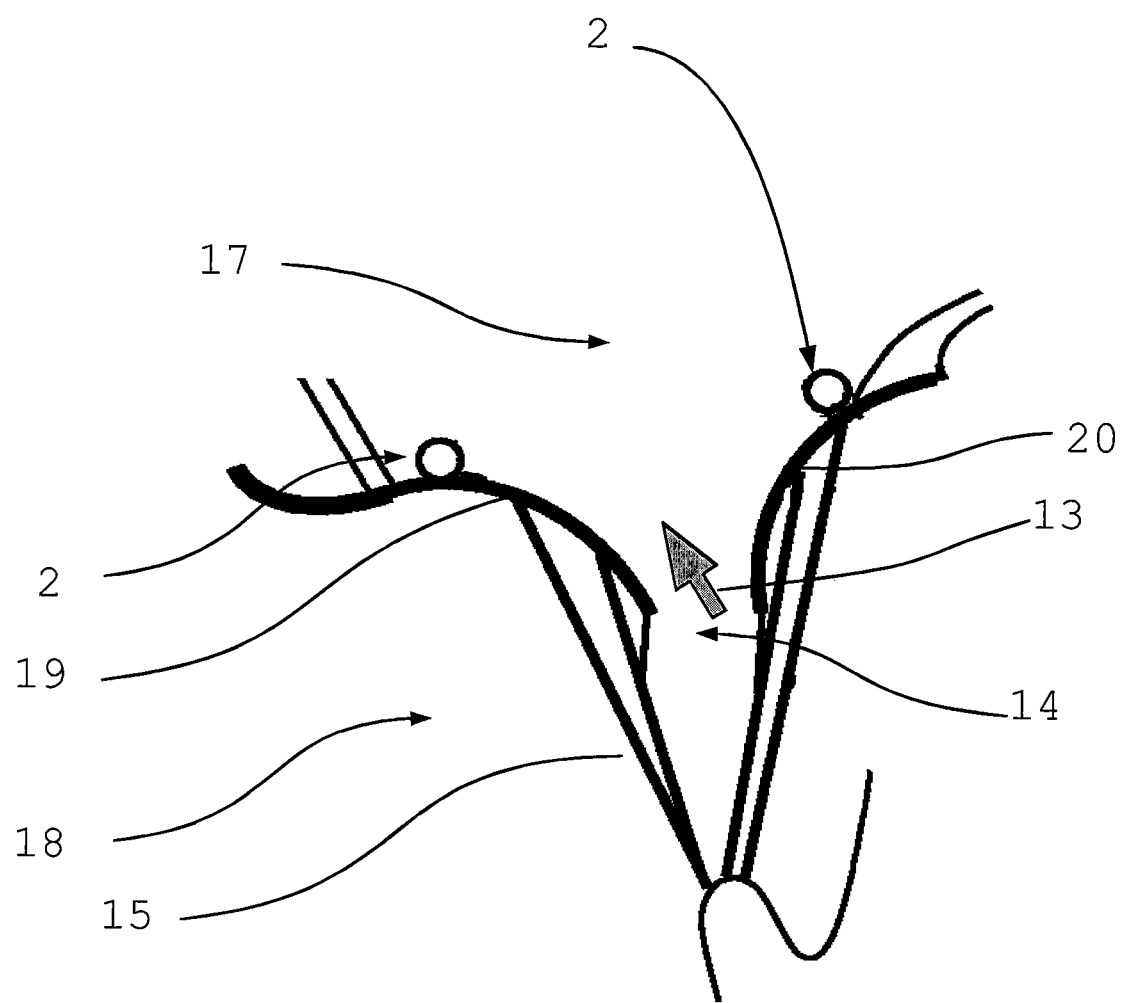

(51) Int. Cl.
    *A61B 8/06*     (2006.01)
    *A61B 8/12*     (2006.01)
    *A61B 8/08*     (2006.01)
    *A61B 5/029*    (2006.01)
    *A61B 5/0265*   (2006.01)
    *A61B 5/0285*   (2006.01)

(52) U.S. Cl.
    CPC ............... *A61B 8/12* (2013.01); *A61B 8/488* (2013.01); *A61F 2/2466* (2013.01); *A61B 5/0265* (2013.01); *A61B 5/0285* (2013.01); *A61F 2250/0002* (2013.01); *A61F 2250/0004* (2013.01)

(58) Field of Classification Search
    CPC ......... A61F 2/2442–2448; A61B 5/686; A61B 8/06; A61B 8/12; A61B 8/488; A61B 5/029; A61B 5/0265; A61B 5/0285
    See application file for complete search history.

(56) References Cited

U.S. PATENT DOCUMENTS

| | | | | |
|---|---|---|---|---|
| 8,545,414 | B2* | 10/2013 | Fitzgerald | A61N 1/36514 600/374 |
| 2005/0060030 | A1* | 3/2005 | Lashinski | A61B 5/6882 623/2.37 |
| 2008/0027483 | A1* | 1/2008 | Cartledge | A61B 5/061 606/201 |
| 2009/0234404 | A1* | 9/2009 | Fitzgerald | A61N 1/36514 607/9 |
| 2011/0301699 | A1* | 12/2011 | Saadat | A61B 17/0401 623/2.4 |
| 2012/0123284 | A1 | 5/2012 | Kheradvar | |
| 2013/0006352 | A1 | 1/2013 | Yaron | |
| 2014/0180126 | A1 | 6/2014 | Millett et al. | |
| 2016/0045312 | A1* | 2/2016 | Braido | A61B 5/02028 623/2.37 |
| 2016/0045316 | A1* | 2/2016 | Braido | A61B 5/6862 623/2.38 |
| 2016/0310077 | A1* | 10/2016 | Hunter | A61B 5/686 |

FOREIGN PATENT DOCUMENTS

| | | |
|---|---|---|
| WO | 2015/058808 A1 | 4/2015 |
| WO | 2015/121075 A1 | 8/2015 |
| WO | 2015158789 A1 | 10/2015 |

OTHER PUBLICATIONS

International Search Report Corresponding to PCT/EP2016/059623 dated Aug. 2, 2016.

Written Opinion Corresponding to PCT/EP2016/059623 dated Aug. 2, 2016.

\* cited by examiner

ANNULOPLASTY SYSTEM AND A METHOD FOR MONITORING THE EFFECTIVENESS OF AN ANNULOPLASTY TREATMENT

The present invention relates to an annuloplasty system and a method for monitoring the effectiveness of an annuloplasty treatment.

Annuloplasty (e.g. mitral or tricuspid annuloplasty) is the implantation of an annuloplasty device (e.g. mitral ring or tricuspid ring) to deform and/or reinforce the valve annulus to correct insufficient valve function. During a classical annuloplasty procedure, the surgeon sizes the valve annulus and chooses an annuloplasty device accordingly. This procedure is performed on the arrested heart with a cardiopulmonary bypass. However, the effectiveness of an implanted annuloplasty device cannot be assessed during the procedure, because the heart is arrested. Only upon restarting the heart is it possible to assess whether the device has had the desired effect to correct valve function.

If the repair has not been successful, the patient has to undergo a second operation. Without the second operation, there remain certain possible long term consequences of a certain level of residual regurgitation. This procedure may improve the outcome of the implantation procedure.

Recently adjustable annuloplasty devices such as in EP 2 468 215 A1 or in WO 2006/012013 A2 have been developed. These annuloplasty devices can be reshaped in vivo which allows a further deformation of the annulus without having to replace the annuloplasty ring. The adjustment of such an annuloplasty ring replaces the second operation and hence reduces the damages from the second operation.

However, the assessment whether the second operation was successful is only possible after a manipulation is completed. This assessment of the function of a heart valve is classically conducted with a transthoracic echocardiogram. The transthoracic echocardiogram is conducted at a distance from the heart valve which limits the resolution of the echocardiogram.

Equipping annuloplasty rings with sensors has been proposed. By way of example, US 2013/0006352 A1, proposes attaching a sensor capable of measuring pressure, temperature or blood velocity to a annuloplasty device. This sensor is a microelectromechanical system (MEMS) and may assist during the implantation procedure or in the years after it. Further during the implantation procedure the utilization of a positioning (xyz) sensor is particularly suggested. This xyz sensor allows an accurate positioning of the annuloplasty device by using an external system that reads the information transmitted from the sensor.

However, the annuloplasty device according to US 2013/0006352 A1 is not adjustable. Thus the information gathered by the sensor can only be utilized to assess whether an explantation is necessary.

The object of the present invention is to overcome the disadvantages of the prior art and in particular to provide an annuloplasty system which allows to assess the effect of a manipulation of an annuloplasty ring assembly when implanted.

In some non-limiting examples, the invention relates to an annuloplasty system comprising a sensor that can measure a regurgitation of a valve. Some non-limiting examples focus on treating atrioventricular cardiac valves such as the mitral valve or the tricuspid valve, but the concept, function and benefit are not limited to these valves.

According to the invention the problem is solved with a system and a method according to the independent claims and their characterizing features.

It is suggested to provide an annuloplasty system comprising an annuloplasty ring assembly, at least one sensor and an external monitor or a prompting device. The annuloplasty ring assembly has an interface adapted to establish an operative connection with a manipulator. The manipulator is utilized for manipulating said annuloplasty ring assembly. The sensor is configured to detect regurgitation. The external monitor or the prompting device is adapted to provide, e.g. display, information based on said detected regurgitation.

As herein used the term "annuloplasty ring assembly" is intended to cover devices utilized to reshape a valve. Preferably the annuloplasty ring assembly is used to reshape a cardiac valve such as the mitral or tricuspid valve. The annuloplasty ring assembly may comprise a tubular ring. This tubular ring is preferably anchored in or sutured to a native heart valve.

The term "manipulation" as used herein is limited to manipulations of the shape and/or size of the annuloplasty ring assembly.

The term "ring" as used herein is intended to cover any shape for circumscribing at least a majority of a periphery of a valve annulus. A ring may be closed (e.g. generally "O" shaped or generally "D" shaped) or a ring may be open (e.g. generally "C" shaped). A ring does cover non round geometries (e.g. "D" shapes, elongated "C" shapes") as well as round geometries (e.g. generally "O" shaped or generally "C" shaped). A ring may be in a non-planar 3D shape, e.g. generally a saddle shape. The ring may be three dimensionally bent "O", "C" or "D" shaped.

The interface adapted to establish an operative connection is preferably adapted to establish a mechanical connection. The mechanical connection is utilized to deform the annuloplasty ring system with the manipulator. Preferably the manipulation is utilized to alter the shape and/or size of a specific section of the annuloplasty ring assembly. Ideally this manipulation then influences the coaptation of leaflets of the valve and thus the regurgitation. Exemplary interfaces suitable for the mechanical manipulation are shown in PCT/EP2013/072378 and PCT/EP2015/051782 which are incorporated herein by reference.

Alternatively the interface is adapted to establish an operative connection where the manipulator transfers heat or electromagnetic waves or magnetic fields or other waves, e.g. ultrasound waves. One embodiment of a manipulation with magnetic fields is shown in U.S. Pat. No. 6,406,493 B1 which is incorporated herein by reference.

Regurgitation refers to a blood flow going through the valve against an intended general direction. This flow leaks through the valve when the valve is closed. For example mitral regurgitation is a flow in a heart from a left ventricle through a mitral valve to a left atrium.

The sensor is configured to detect regurgitation. Regurgitation may be detected by the sensor by measuring a physical parameter generated by the regurgitation or by measuring a parameter, which is modified by the regurgitation. This parameter may be generated by the annuloplasty system or by an external source. The sensor preferably measures speed and direction of the regurgitation. Alternatively the sensor measures other physical quantities related to regurgitation such as pressure or sound.

The external monitor or prompting device is adapted to provide information based on the detected regurgitation. The external monitor may be connected or connectable with a wire or wirelessly to the sensor.

In case of a wire connection, the sensor might be connected to the monitor over the wire, i.e. a transmission line preferably connecting the monitor to a connector of the annuloplasty ring and connecting means connecting the sensor to the connector and hence the transmission line.

Additionally the external monitor or the prompting device may compare the regurgitation of the valve before and after a manipulation of the annuloplasty ring assembly and may inform a user of the annuloplasty device, e.g. a surgeon, based on the differences.

A user, who manipulates the annuloplasty ring assembly, can monitor the impact of his manipulation on the external monitor. Thereby direct feedback on the effectiveness of his treatment is provided. This allows an optimal reshaping of the annuloplasty ring assembly and thus an improved patient outcome. Furthermore the evaluation of the effectiveness becomes easier and faster during the adjustment procedure.

Preferably, the sensor comprises a Doppler-effect sensor to measure the regurgitation of the heart valve. The Doppler-effect allows a non-contact measurement of the regurgitation. Further, the Doppler-effect can be utilized to measure flow velocities at a distance from the sensor.

Preferably, the sensor comprises an ultrasound transducer. The ultrasound transducer can generate ultrasound waves as well as detect an ultrasonic echo. The ultrasound transducer preferably measures the regurgitation with the Doppler-effect. The ultrasound transducer generates an ultrasound beam or pulse. The beam or pulse interacts with the regurgitation and is reflected to the ultrasound transducer, where the pulse or beam is detected. Alternatively an ultrasonic transmission measurement, which uses transit times of the ultrasound waves to calculate an average flow velocity, can be utilized.

In one embodiment the sensor may comprise a magnetic flow meter. The magnetic flow meter such as a Hall effect sensor measures the regurgitation with a potential across a cross-section of the valve. A magnetic field, e.g. an alternating magnetic field, may be generated electromagnetically by the annuloplasty system. The magnetic fields may be generated by a solenoid part of the annuloplasty ring or part of the catheter.

In case the solenoid is part of the annuloplasty ring, the solenoid may be wound around the ring or is arranged in the annuloplasty ring. An electric current is applied to the solenoid through the connector. This AC or DC current induces an oscillating or constant magnetic field. Regurgitated blood acts as moving electrical conductor and interacts with the magnetic field. Thus, an electromotive force is generated which may be detected with electrodes. The electrodes send a signal containing information on the regurgitation to the connector and to the monitor.

In case the solenoid is part of the catheter, the solenoid may be wound around the catheter having a kind of C-shaped tip to have the solenoid partly around the annulus. Alternatively, the solenoid is arranged in the catheter in a C-form in a C-shaped tip.

Alternatively the magnetic field may be generated with permanent magnets comprised by the annuloplasty system, i.e. the annuloplasty ring or the catheter. The magnetic field is applied basically perpendicular to the blood flow.

The blood flow acts as a moving electrical conductor, which interacts with the magnetic field. As a result an electromotive force is induced. The induced electromotive force is related to the regurgitation. Said electromotive force is measured across a direction essentially perpendicular to the flow direction of the blood and essentially perpendicular to the magnetic field.

Alternatively, the change of the signal generated by the solenoid and the regurgitation may be measured with any of the electrical parameters (tension, current or resistance). Another indirect alternative may be a measurement of the variations of the magnetic field.

Alternatively, said sensor comprises a light conductor, e.g. an optical fiber. The light conductor guides light, e.g. monochromatic light, to the place where regurgitation is expected. The light interacts with the regurgitation and is reflected or scattered back to the light conductor/sensor. Alternatively, a second light conductor is utilized to detect the scattering.

The light is reflected or scattered back in a specific way if regurgitation is present. On the basis of this reflected or scattered back light, the sensor is able to detect if regurgitation is present. A detection of the regurgitation with light offers a fast measurement of the regurgitation. Additionally, the light conductor may allow a space saving design of the sensor. According to a further alternative embodiment a micro camera might be applied on the ring or a catheter. Also, instead of using an optical fibre for transmission of light a fibre could be used for imaging using a camera outside of the body.

Preferably, the sensor comprises means to measure a spatial distribution of a flow velocity. Preferably the spatial resolution is measured by a 1D phased array of ultrasound transducers and/or by sweeping the ultrasound transducer through a series of positions. The spatial resolution allows a localization of the "leaks" in the valve.

Therewith, the manipulation procedure of the annuloplasty ring assembly can be adapted to reshape the mitral valve accordingly. Particularly, reshaping of the annuloplasty ring assembly in distinct places that are determined with the spatial distribution the flow velocities is advantageous.

Preferably, the sensor is connected to or connectable to or is part of the annuloplasty ring assembly. The sensor is preferably situated at a location suited for measuring the regurgitation. The sensor may be permanently connected to the annuloplasty ring assembly. A permanent connection would allow a long term monitoring of the functioning of the valve.

Alternatively the sensor may be introduced after an implantation of the annuloplasty ring assembly for use during manipulation and/or removed after a manipulation procedure of the ring assembly. Thereby, the complexity of the annuloplasty ring assembly is reduced.

Preferably, the annuloplasty system comprises a delivery device connected or connectable to said interface, wherein the delivery device is adapted to deliver said manipulator.

The delivery device, e.g. a catheter, is preferably adapted to enter the annuloplasty assembly. Within the assembly the catheter is connectable to the interface where the interface is manipulated with heat or mechanical pressure or electrically or magnetically.

A "catheter" as used herein is intended refer to any flexible tubular structure suitable for medical applications adapted to provide a physical connection between the outside of the patient's body and the annuloplasty ring assembly.

Alternative delivery devices may include but are not limited to tweezers or guide wires.

The delivery device is preferably removable and preferably adapted to reshape the annuloplasty assembly. This allows a simple and versatile annuloplasty ring assembly.

Preferably, the delivery device has a signal connector, which can connect said sensor to the external monitor. Through the connector the information read out by the sensor becomes available to the external monitor. The connector may connect to the monitor with a wire or wirelessly.

Preferably, the system comprises a mechanical connector, preferably on a common unit with the signal connector. Such a mechanical connector establishes a connection between the manipulator and the user. The delivery device is preferably introduced through the mechanical connector.

Alternatively, the connector can be utilized to actuate the delivery device, which may be comprised within the mechanical connector.

In one embodiment the delivery device includes the sensor. The sensor may be placed flexibly and repositioned if advantageous because the delivery device can be positioned as desired. An additional advantage is that the delivery device comprises the tools to manipulate the annuloplasty as well as the tools to assess the success of the manipulation in one device.

Alternatively, the delivery device as well as the annuloplasty ring assembly each includes at least one sensor. In such a setup at least one sensor could act as a sender and at least one sensor could act as a receiver.

Preferably, the manipulator includes the sensor.

Preferably, the manipulator comprises an inflatable balloon. Preferred embodiments of the manipulator and delivery device comprising the inflatable balloon and the sensor are described in US 2014/0180126 A1, which is incorporated herein by reference. Inflatable balloons comprised by a catheter are simple and versatile manipulators.

The sensor may be placed directly on the balloon. Alternatively, the sensor may be positioned on a tip of a balloon or on the connecting line used to inflate the balloon. The tip of the balloon may be separate part, comprised by the connecting line or may be part of the balloon. A placement of the sensor on the tip or the catheter has the advantage that it does not expose the sensor to the expansion of the balloon.

Preferably the annuloplasty system comprises a closed loop control system adapted to monitor the change in regurgitation and adapted to manipulate the adjustable ring in dependence of the monitored changes. In the closed loop control system the regurgitation is measured and compared to a threshold. The control system controls the manipulator. The manipulator manipulates the annuloplasty ring assembly such that a difference between the measured regurgitation and the threshold is minimal. The control system automatically manipulates the assembly and thus a user interaction is minimal.

The invention further relates to a method of monitoring the effectiveness of an annuloplasty treatment. In the method an annuloplasty system is provided. The annuloplasty system comprises an annuloplasty ring assembly, at least one sensor and an external monitor or prompting device. The sensor is configured to detect regurgitation. The external monitor or the prompting device is configured to display information based on the regurgitation detected by the sensor. The annuloplasty ring assembly is manipulated with the manipulator. The regurgitation is detected with said sensor and information based on said detected regurgitation with said monitor or prompting device is provided. If said detected regurgitation is above a threshold the adjustment is repeated. If regurgitation is below the threshold the manipulation is stopped. Therewith the manipulation is directly controlled and only performed in an adequate quantity.

Figure 2:
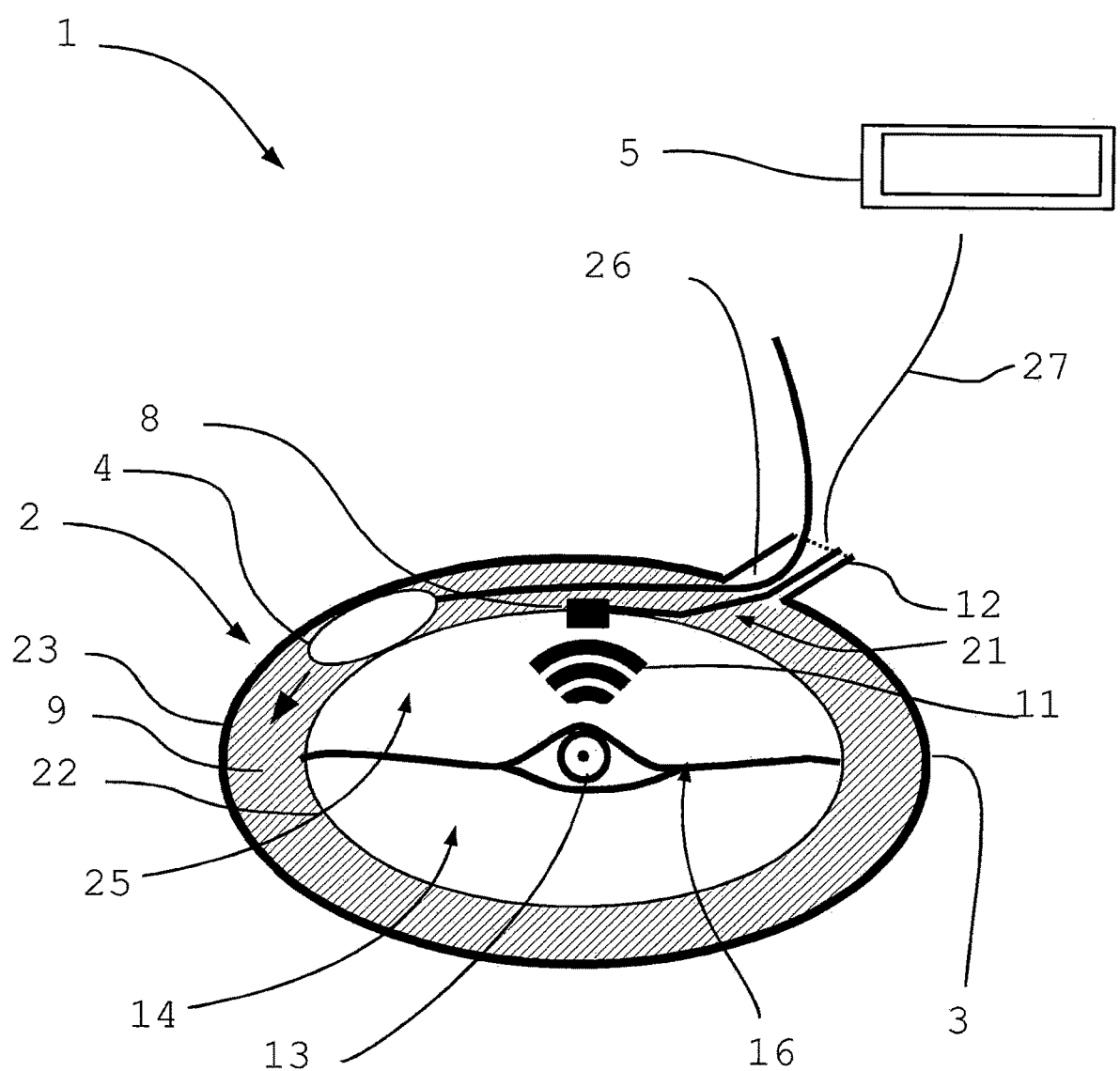
Figure 3:
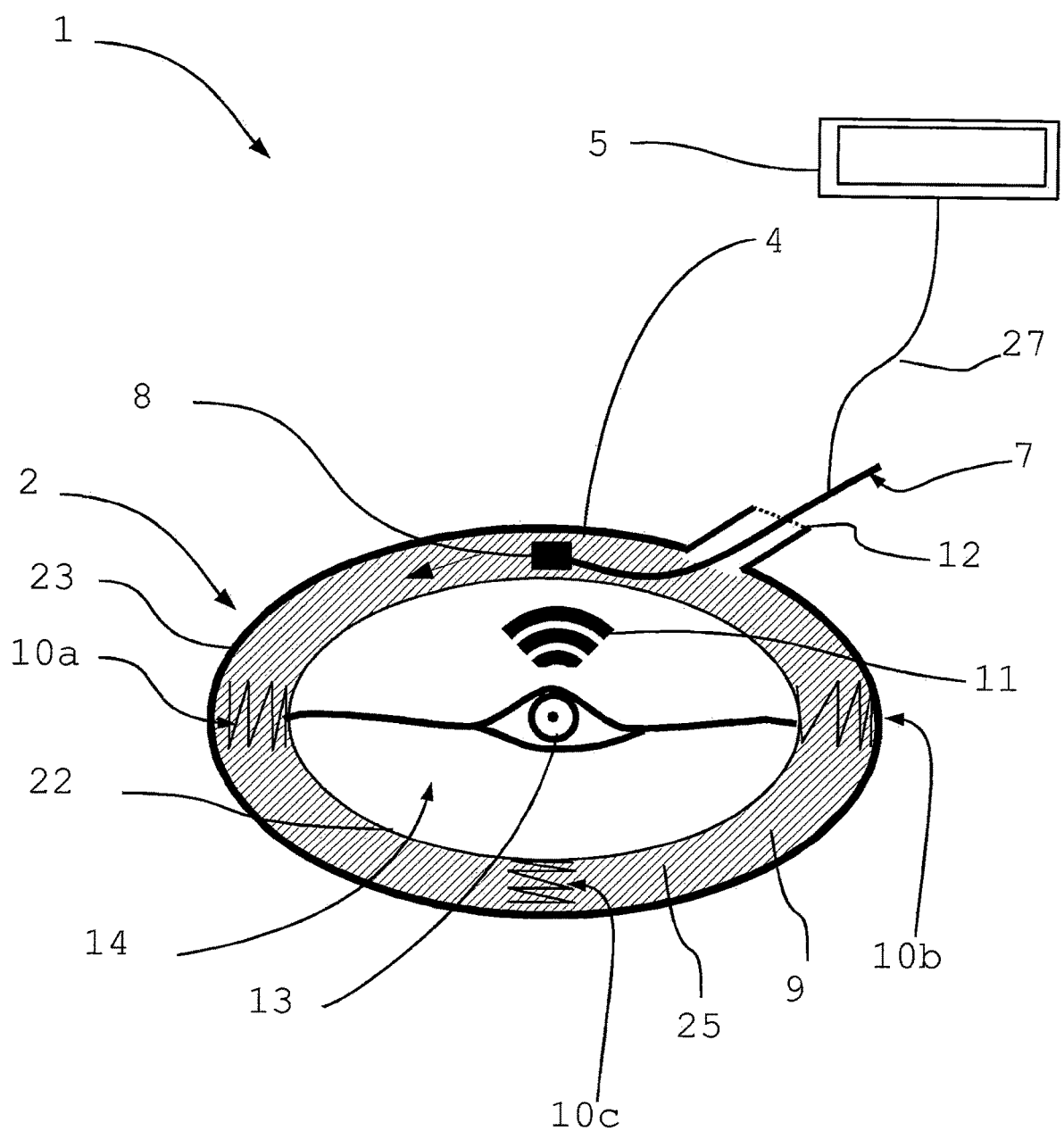
Figure 4:
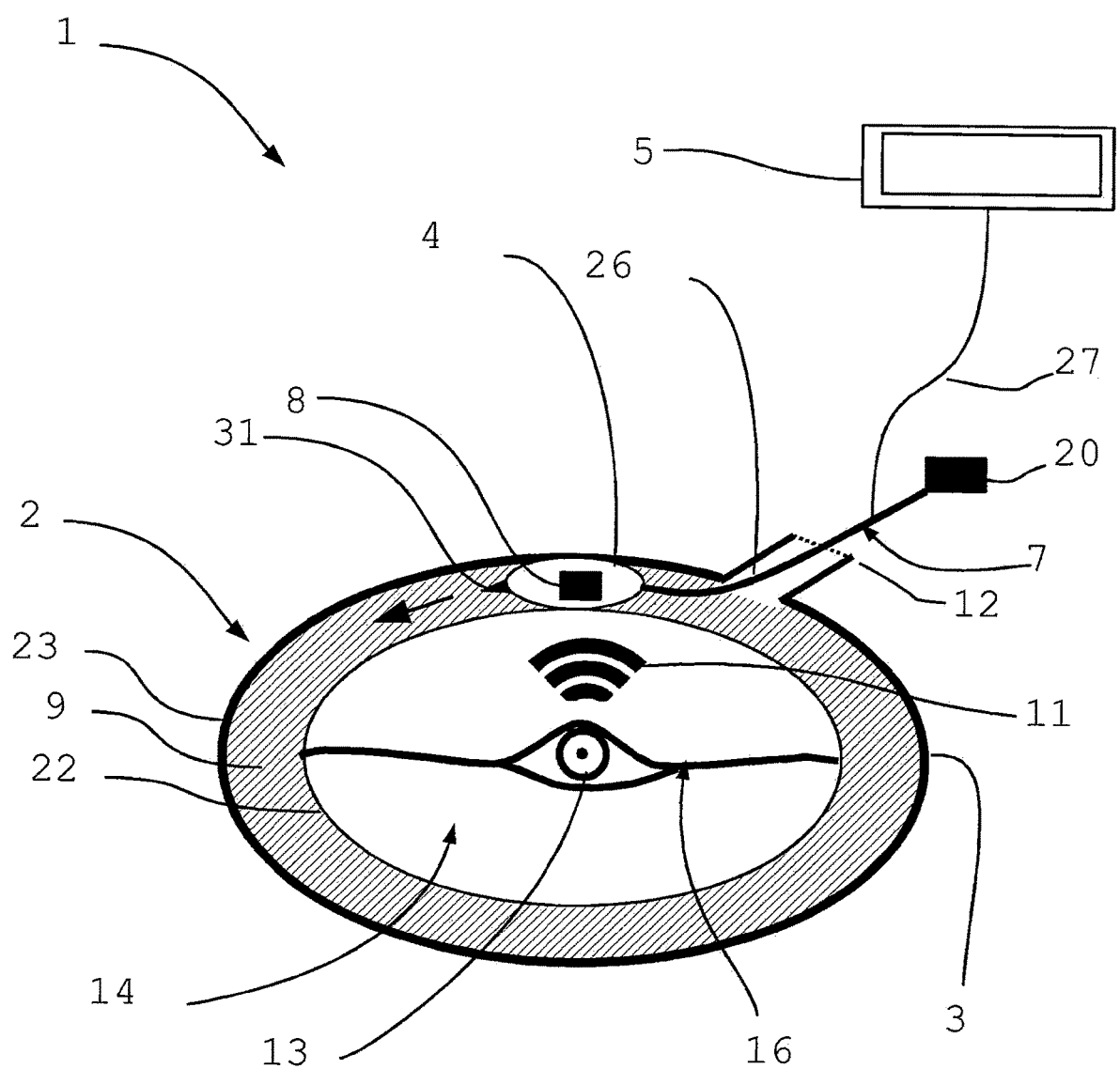
Figure 5:
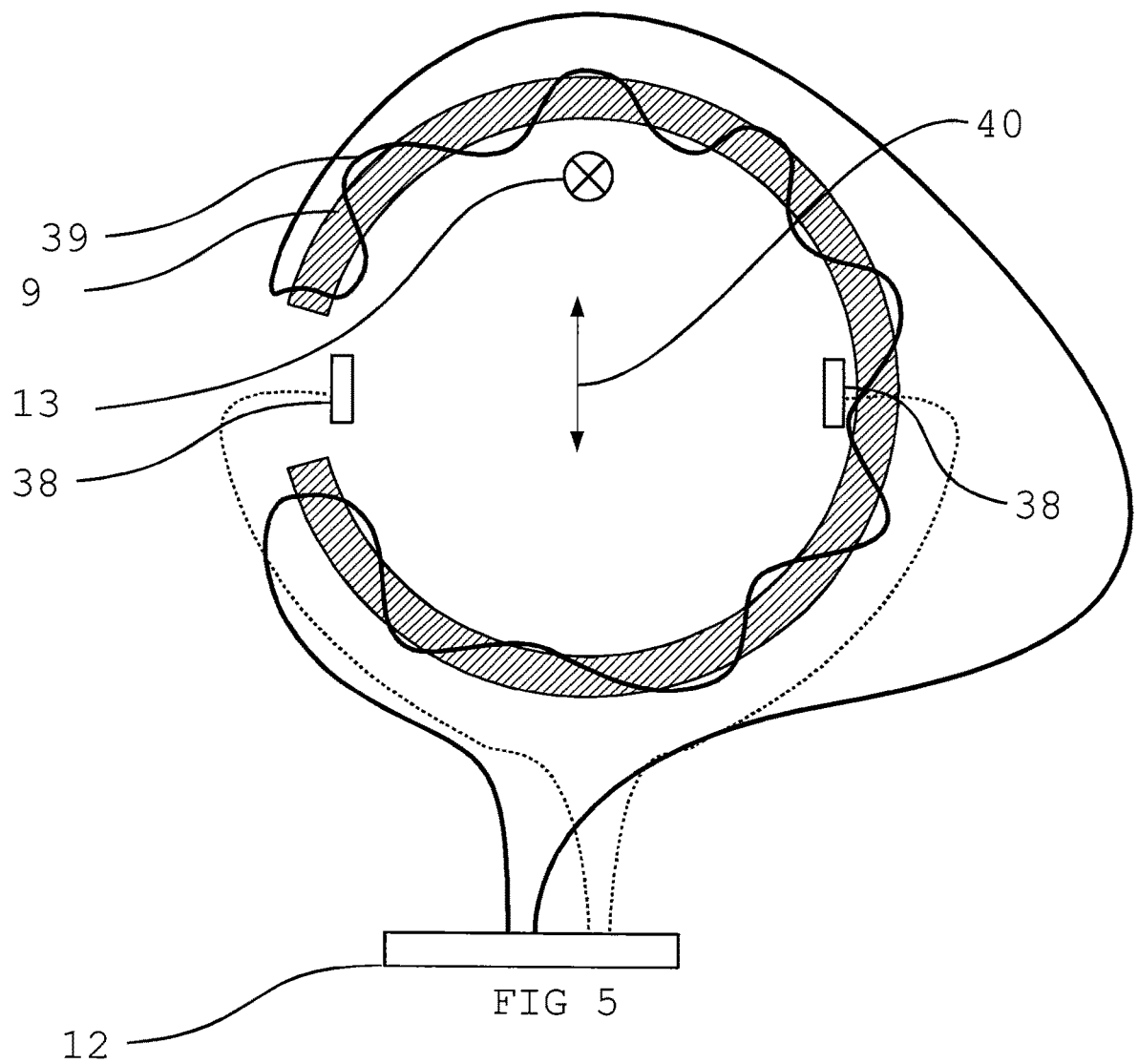
Figure 6:
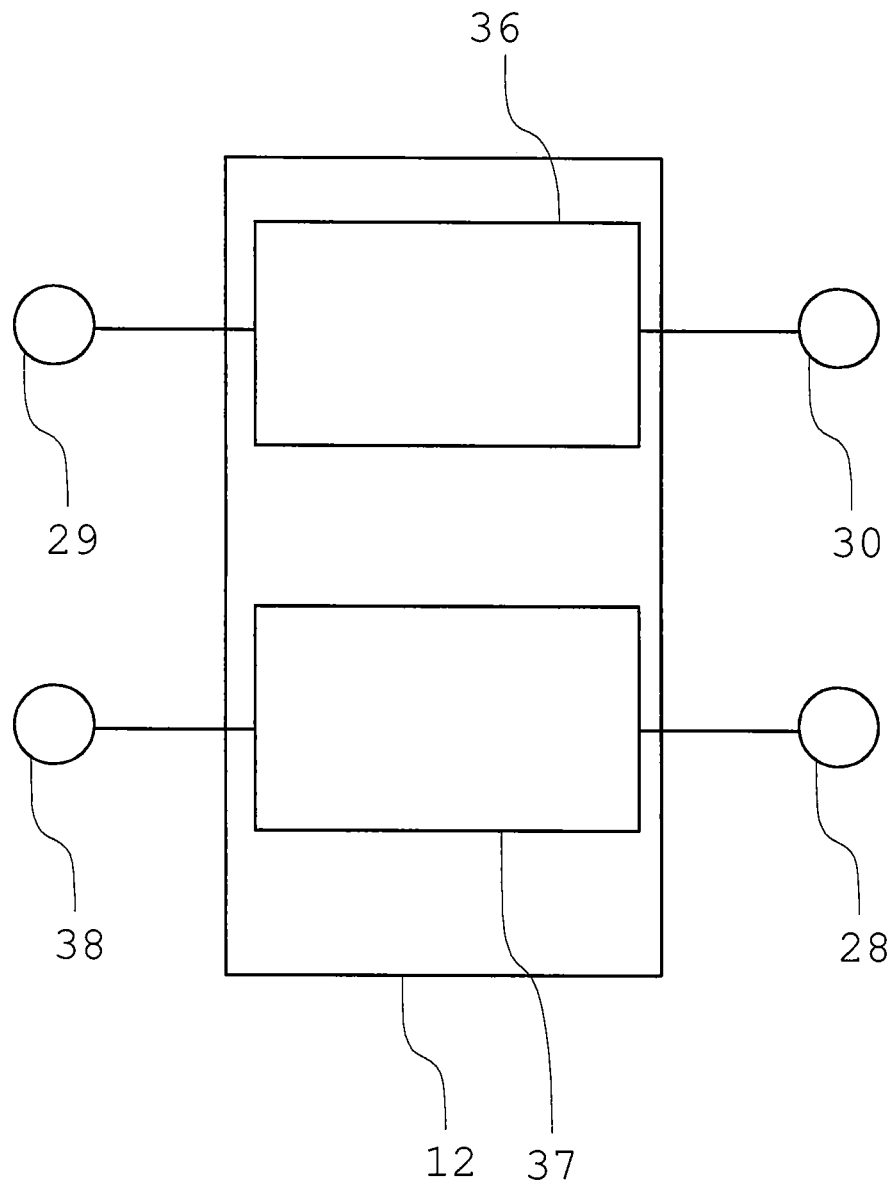
Figure 7:
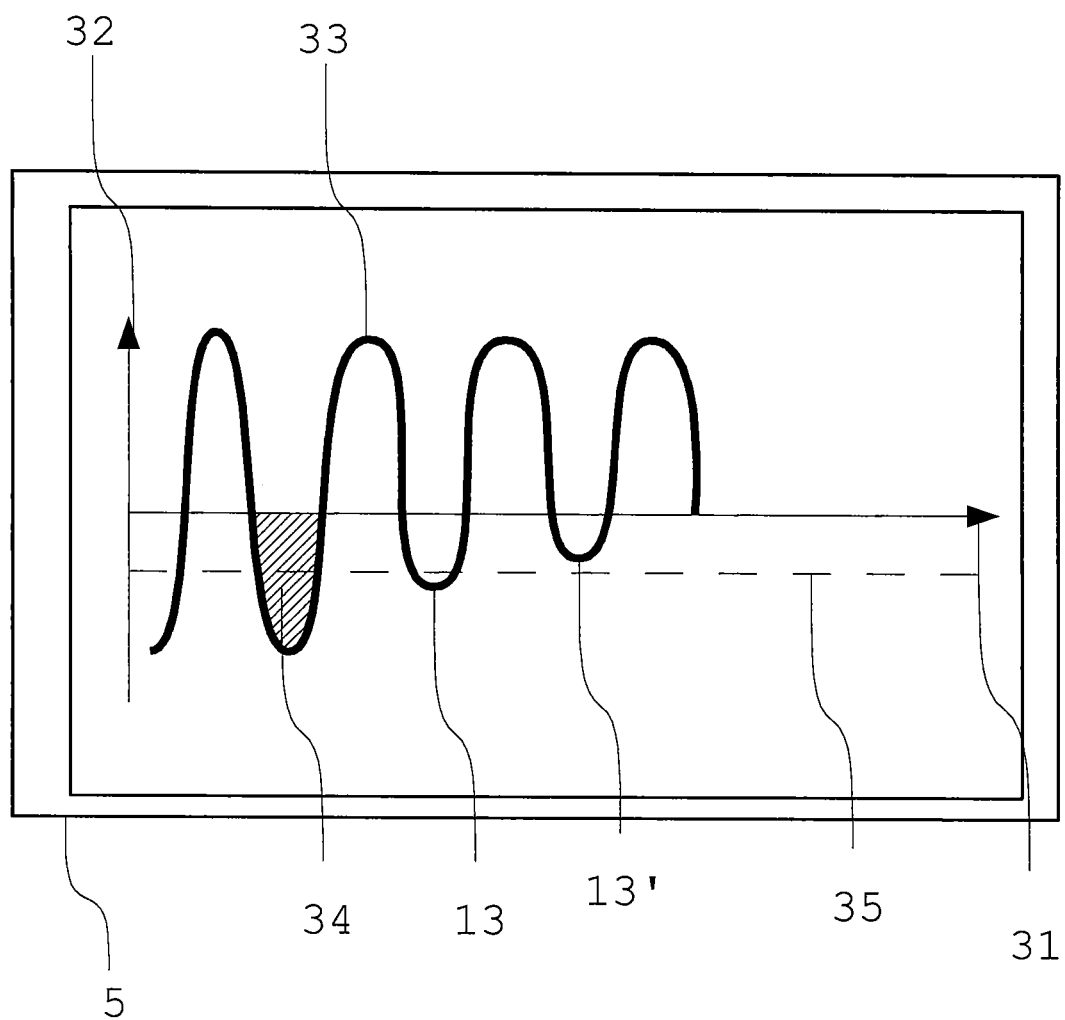

Non-limiting embodiments of the invention are described, by way of example only, with respect to the accompanying drawings, in which:

FIG. 1: is a schematic view of a mitral valve with regurgitation and an annuloplasty ring assembly, FIG. 2: is a schematic view of a first embodiment of an annuloplasty system according to the invention, FIG. 3: is a schematic view of a second embodiment of an annuloplasty system according to the invention, FIG. 4: is a schematic view of a third embodiment of an annuloplasty system according to the invention, FIG. 5 is a schematic view of a fourth embodiment of an annuloplasty system according to the invention, FIG. 6: is a schematic view of a connector according to the invention, FIG. 7: is a schematic representation of an output of an external monitor.

FIG. 1 shows a cross-section schematic view of a mitral valve 14 with regurgitation 13 and an annuloplasty ring assembly 2. The annuloplasty ring assembly 2 is used to manipulate the mitral valve 14. The mitral valve 14 regulates a blood flow from an atrium 17 to a ventricle 18. Thereby a functioning mitral valve 14 allows only a flow from the atrium 17 to the ventricle 18. During systole when the pressure in the ventricle 18 is higher than in the atrium 17, the mitral valve 14 closes. The mitral valve 14 closes with an anterior leaflet 19 and a posterior leaflet 20. The leaflets 19, 20 coapt and therewith prohibit a flow from the ventricle 18 to the atrium 17. The leaflets 19, 20 are held by tendinous chords 15, which hold the leaflets on the ventricular side.

Certain medical conditions cause the leaflets 19, 20 to coapt insufficiently causing a regurgitation 13. The regurgitation 13 is a back flow of blood from the ventricle 18 through the mitral valve. In order to re-establish proper mitral valve functioning, the annuloplasty ring assembly 2 reshapes the mitral valve 14. Thereby, the coaptation of the leaflets 19, 20 is improved the regurgitation 13 reduced or stopped.

FIG. 2 shows a schematic view of a first embodiment of an annuloplasty system 1. In this embodiment a sensor 8 is part of an annuloplasty ring assembly 2. The sensor 8 is connected with the external monitor 5 via connection means 21, a connector 12 and the transmission line 27.

The annuloplasty ring assembly 2 is arranged as an annular ring with an oval shape which is formed by a tube 9 with a "D" shaped or circular cross section. For a better understanding of the tube 9, the upper half of the tube 9 directed to the viewer is shown transparently. The tube 9 is made out of Nitinol. An outer wall 23 of the tube 9 is thicker than an inner wall 22 of the tube 9. Through this increased thickness of the outer wall 23 compared to the inner wall 22, the outer wall 23 is more rigid than the inner wall 22. Thereby the inner wall forms an interface through which the annuloplasty ring assembly may be manipulated. Especially the annuloplasty ring assemblies from PCT/EP2013/072378 and PCT/EP2015/051782 are suitable.

The sensor 8 comprises an ultrasound transducer and measures the regurgitation 13 of the mitral valve 14. The ultrasound transducer sends a pulse in the direction of the back flow. The back flow modifies the pulse.

A reflection 11, which compromises information related to the regurgitation, is sent back to the sensor 8 via a transmission line 27. The transmission line 27 may transmit particularly optical signals, electrical signals and/or pressure. The sensor 8 detects the reflection and deduces the information related to the regurgitation. A signal of the sensor 8 is transmitted to the connector 12 over connecting means 21. From the connector 12 the signal is sent with the transmission line 27 to the external monitor 5. The external monitor 5 then displays the regurgitation 13 to a user.

A catheter 7 is introduced into the tube 9 through the connector 12. The catheter is then arranged between the outer wall 23 and the inner wall 22. The catheter 7 comprises an inflatable balloon 4. The balloon 4 is moveable around the circumference of the tube 9 (indicated with an arrow).

The balloon 4 is expandable with gas or a liquid. The gas or liquid is provided by an actuator 20 over a connecting line 26. When inflated with gas, the balloon 4 expands and displaces the inner wall 22 inwardly towards an inside area 25 of the tube 9. Through the displacement of the inner wall 22, the mitral valve 14, to which the assembly 2 is applied, is adjusted. Due to the plastic deformation of the tube, the inwardly displaced wall remains in its expanded position. Ideally this manipulation of the assembly 2 causes a change in the coaptation 16 of the mitral valve leaflets 19, 20 (see FIG. 1) and consequently a change in regurgitation. A new regurgitation 13' (see FIG. 7) is measured by the sensor 8 and compared to a previous regurgitation 13 and to a predefined threshold 35 (see FIG. 7). The new regurgitation 13' and the change in regurgitation are displayed on the external monitor. In case the regurgitation has not decreased below the predefined threshold, a user may decide now whether she wants to inflate the balloon 4 further. Alternatively the user may deflate the balloon 4 and move the balloon 4 to another place, where the balloon 4 may be inflated again. The inner wall 22 may therewith be displaced at multiple parts. At each displacement the success of the manipulation is monitored with the external monitor 5. Once the regurgitation decreases below the predefined threshold 35 (see FIG. 7), the balloon 4 is removed from the tube 9.

FIG. 3 shows a schematic view of a second embodiment of the adjustable annuloplasty system 1. In the second embodiment the sensor 8 is comprised by the catheter 7. The catheter 7 is introduced into the tube 9 through a connector 12 and moveable around the circumference of the annuloplasty ring assembly 2 (indicated with an arrow). The sensor 8 comprises an optical fiber and measures the regurgitation 13 of the mitral valve 14. The optical fiber emits the optical signal at an end of the optical fiber. in the direction of the back flow. The optical signal is reflected by the blood, e.g. red blood cells.

An optical reflection 11, which compromises information related to the regurgitation, is sent back to the sensor 8. The sensor 8 detects the reflection and deduces the information related to the regurgitation. A signal of the sensor 8 is transmitted with the transmission line 27 to the external monitor 5. The external monitor 5 may process signal further. The external monitor 5 then displays the regurgitation 13 to a user. The user can then choose to manipulate the annuloplasty ring assembly with a balloon 4 (see FIG. 1).

The annuloplasty ring assembly is adjustable with a different mechanism in this embodiment. Three actuation elements 10a, b, c are arranged in the tube 9 between the inner wall 22 and the outer wall 23. Two actuation elements 10a, b are arranged at lateral portions of the tube 9, one actuation element 10c is arranged at a posterior portion of the tube 2. The three actuation elements 10 each comprise a stent. The stents have a section integrally formed with the outer wall 23. The stents are expandable with a balloon 4 (see FIG. 2). The three stents may be expanded with the same balloon or with a separate balloon each. The balloon is inflated via the connecting line 26 (see FIG. 2). The stents expand inwardly because of the part integrally formed with the outer wall 23 is more rigid than the rest of the stent. The stents therefore displace the inner wall 22 inwardly and adjust the mitral valve leaflets 19, 20. The adjustment mechanism of the assembly 2 can be utilized independent of the positioning of the sensor 8. For example the actuation elements 10a-c in FIG. 3 may be utilized in the embodiments shown in FIGS. 2 and 4.

FIG. 4 shows a schematic view of a third embodiment of an annuloplasty system 1. In this embodiment the sensor 8 is comprised by the balloon 4. The sensor 8 comprises an ultrasound transducer and measures the regurgitation 13 of the mitral valve 14. The ultrasound transducer sends a pulse in the direction of the back flow. The back flow modifies the pulse. A reflection 11, which compromises information related to the regurgitation, is sent back to the sensor 8. The sensor 8 detects the reflection and deduces the information related to the regurgitation. A signal of the sensor 8 is transmitted with the transmission line 27 to the external monitor 5. The external monitor 5 may process signal further. The external monitor 5 then displays the regurgitation 13 to a user. The user can modify the annuloplasty ring assembly 2 directly thereafter with the balloon 4.

Of course, any kind of sensor as disclosed herein might be part of any element of the annuloplasty system as described herein. Hence, the balloon might e.g. comprise an optical sensor or the catheter an ultrasound transducer etc.

FIG. 5 shows a schematic view of a fourth embodiment of an annuloplasty system according to the invention. In this embodiment a solenoid 39 is wound around the tube 9. The tube according to FIG. 5 is an open ring such. An electric current is applied to the solenoid 39 through connector 12. This AC or DC current induces an oscillating or constant magnetic field 40. A regurgitation 13, e.g. a regurgitation of blood, acts as moving electrical conductor and interacts with the magnetic field 40. Thus, an electromotive force is generated which may be detected with electrodes 38. The electrodes 38 send a signal containing information on the regurgitation 13 to the connector 12.

FIG. 6 shows a schematic view of the connector 12. The connector comprises two parts: a signal connector 36 and a mechanical connector 37. The signal connector 36 is connected to the sensor with a sensor connection port 29 and to the external monitor with a monitor connection port 30. The mechanical connector 37 establishes an operative connection between an actuator connection port 28 and a manipulator connection port 38. Both connection ports 38 and 29 may be connectable or connected or part of to the connecting line 26.

FIG. 7 shows a schematic representation of an output of an external monitor 5. The external monitor 5 displays a flow velocity on the y axis 32 and a time on the x-axis 31. The flow velocity may be measured at a particular location or an average velocity over the cross-section of the valve. Preferably, the flow velocity at the position of the regurgitation is displayed. A positive flow 33 represents the blood flowing in the intended direction. A negative flow represents the regurgitation 13. An integration over the negative flow may indicate the volume 34 of blood that flows back. The user would identify the regurgitation 13 on the monitor. Then the user would manipulate the annuloplasty ring assembly 2 (see FIG. 2). Ideally the manipulation would improve the coaptation 16 (see FIG. 2) and thus the regurgitation 13 and the volume 34 would decrease. The user would continue to manipulate until the regurgitation 34 drops below a threshold 35. Alternatively or additionally a threshold for the volume could be displayed.

The invention claimed is:
1. An annuloplasty system comprising:
an annuloplasty ring assembly having an interface adapted to establish an operative connection with a manipulator for manipulating said annuloplasty ring assembly, and comprising an adjustable tube extending circumferentially, at least one sensor configured to detect a regurgitation of a valve, and an external monitor adapted to provide information based on said detected regurgitation, wherein the sensor is part of the annuloplasty ring assembly and wherein the sensor comprises a magnetic flow meter, wherein the magnetic flow meter comprises a solenoid in the annuloplasty ring assembly and wound around the tube for electromagnetically generating a magnetic field from an electric current applied to the solenoid, and a Hall effect sensor, adapted to measure an electromotive force resulting from blood flow perpendicular to the generated magnetic field.

2. The system according to claim 1, further comprising a delivery device connected or connectable to said interface, wherein the delivery device is adapted to deliver said manipulator.

3. The system according to claim 2, wherein the delivery device has a signal connector for connecting said sensor to an external monitor adapted to display said information based on said detected regurgitation.

4. The system according to claim 1, further comprising a mechanical connector on a common unit with the signal connector.

5. The system according to claim 2, wherein said delivery device includes said sensor.

6. A method of monitoring an effectiveness of an annuloplasty treatment, the method comprising the steps of:
a) providing an annuloplasty system having an annuloplasty ring assembly, at least one being part of the annuloplasty ring assembly sensor to detect regurgitation, wherein the annuloplasty ring assembly comprises an adjustable tube extending circumferentially and a solenoid wound around the tube, wherein said sensor comprises a magnetic flow meter, wherein the magnetic flow meter comprises a Hall effect sensor, and an external monitor or prompting device to provide information based on said detected regurgitation,
b) manipulating the annuloplasty ring assembly with a manipulator,
c) detecting regurgitation with said sensor, by electromagnetically generating a magnetic field within the annuloplasty ring assembly by applying an electrical current to the solenoid, and measuring an electromotive force resulting from blood flow perpendicular to the generated magnetic field,
d) providing information based on said detected regurgitation with said monitor, and
e) if said detected regurgitation is above a threshold, again starting with step b) or, if said detected regurgitation is below a threshold, stopping manipulation of the ring assembly.

7. The method of claim 6, wherein step (c) comprises applying an electrical current selected from (i) an AC current to generate an alternating magnetic field, or (ii) a DC current to generate a constant magnetic field.

8. The method of claim 6, wherein the solenoid is wound in a circumferential direction of the annuloplasty ring assembly.

9. The system of claim 1, wherein the solenoid is wound in a circumferential direction of the annuloplasty ring assembly.

10. The system of claim 1, wherein the electrical current is selected from (i) an AC current to generate an alternating magnetic field, or (ii) a DC current to generate a constant magnetic field.

* * * * *